United States Patent [19]

Yewer, Jr.

[11] Patent Number: 5,591,122
[45] Date of Patent: Jan. 7, 1997

[54] CONVERTIBLE SUPPORT BELT

[76] Inventor: Edward H. Yewer, Jr., 6259 N. Highway 83, Hartland, Wis. 53029

[21] Appl. No.: 273,524
[22] Filed: Jul. 11, 1994
[51] Int. Cl.$^6$ ..................................................... A61F 5/00
[52] U.S. Cl. .................. 602/19; 2/44; 2/312; 128/100.1; 128/101.1
[58] Field of Search .................................. 602/19; 2/311, 2/312, 44, 300; 128/96.1, 101.1, 102.1, 100.1

[56] References Cited

U.S. PATENT DOCUMENTS

| | | |
|---|---|---|
| 75,737 | 3/1868 | Crocker . |
| 2,181,689 | 11/1939 | Bell . |
| 3,568,670 | 3/1971 | Gaylord, Jr. . |
| 3,603,316 | 9/1971 | Lehman . |
| 4,080,962 | 3/1978 | Berkeley . |
| 4,175,553 | 11/1979 | Rosenberg . |
| 4,366,804 | 1/1983 | Abe ........................ 126/263 |
| 4,475,543 | 10/1984 | Brooks et al. . |
| 4,572,167 | 2/1986 | Brunswick . |
| 4,627,109 | 12/1986 | Carabelli et al. .............................. 2/44 |
| 4,747,399 | 5/1988 | Glomstead . |
| 4,782,535 | 11/1988 | Yewer, Jr. et al. .......................... 2/321 |
| 4,833,730 | 5/1989 | Nelson ........................................ 2/44 |
| 4,836,194 | 6/1989 | Sebastian et al. . |
| 4,907,576 | 3/1990 | Curlee . |
| 4,964,401 | 10/1990 | Taigen . |
| 4,968,027 | 11/1990 | Anderson ................................ 272/123 |
| 4,991,573 | 2/1991 | Miller . |
| 5,036,864 | 8/1991 | Yewer, Jr. et al. ...................... 128/876 |
| 5,179,942 | 1/1993 | Drulias et al. .......................... 602/19 X |
| 5,207,636 | 5/1993 | Striano ..................................... 602/19 |
| 5,267,947 | 12/1993 | James et al. ............................. 602/19 |
| 5,334,134 | 8/1994 | Saunders ................................. 602/19 |
| 5,351,340 | 10/1994 | Aldridge ..................................... 2/108 |
| 5,387,183 | 2/1995 | Jones ....................................... 602/19 |

OTHER PUBLICATIONS

Applicant's Exhibit Nos. 1A and 1B, photographs of and Applicant's Exhibit No. 1C, copy of an advertising insert for, an admitted prior art belt which is commercially available from Valeo, Inc., Waukesha, Wisconsin.

Applicant's Exhibit Nos. 2A and 2B, photographs of admitted prior art belt labelled "UltraActive" and WRS SportsMed Waco Texas USA Made in Tawain.

Applicant's Exhibit Nos. 3A and 3B, photographs of and Applicant's Exhibit 3C and 3D, copy of an advertising insert for, an admitted prior art belt which is commercially available from Tru–Fit® Sports Medicine, Lynn, Massachusetts.

Applicant's Exhibit Nos. 4A, 4B and 4C, photographs of, and Applicant's Exhibit Nos. 4D and 4E, copy of the front and back of a box for, an admitted prior art belt which is commercially available from Sansho Co., Ltd., Osaka, Japan; Applicant's Exhibit No. 4F, a 3 page description of this product and Applicant's Exhibit No. 4G, a 5 page instructional brochure for this product.

Applicant's Exhibit Nos. 5A and 5B, photographs of, and Applicant's Exhibit Nos. 5C and 5D, copy of the front and back of a box for, an admitted prior art belt labelled "Pro" and Pro Orthopedic Services, Inc. Made in USA.

Applicant's Exhibit Nos. 6A, 6B and 6C, photographs of an admitted prior art belt and lumbar pad insert which is commercially available from Valeo, Inc., Waukesha, Wisconsin.

Primary Examiner—Richard J. Apley
Assistant Examiner—Kim M. Lee
Attorney, Agent, or Firm—Quarles & Brady

[57] ABSTRACT

A convertible abdominal support belt for securing around the waist of a user has an insulator insert panel for adding warmth to the user which may be removed when coolness is desired.

4 Claims, 3 Drawing Sheets

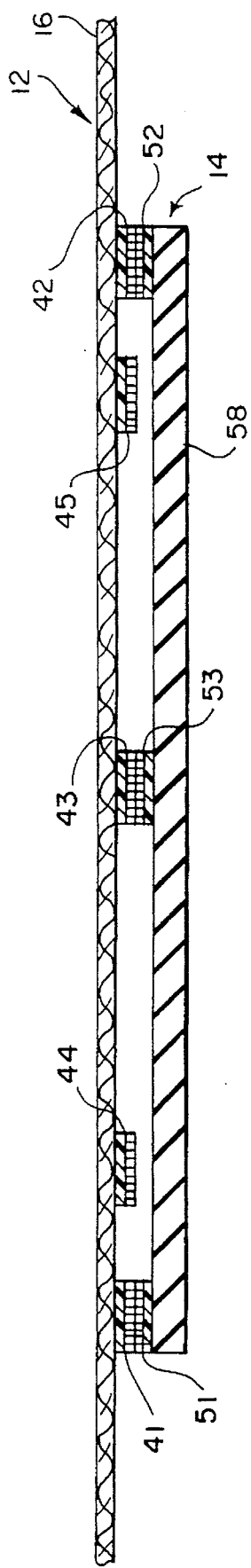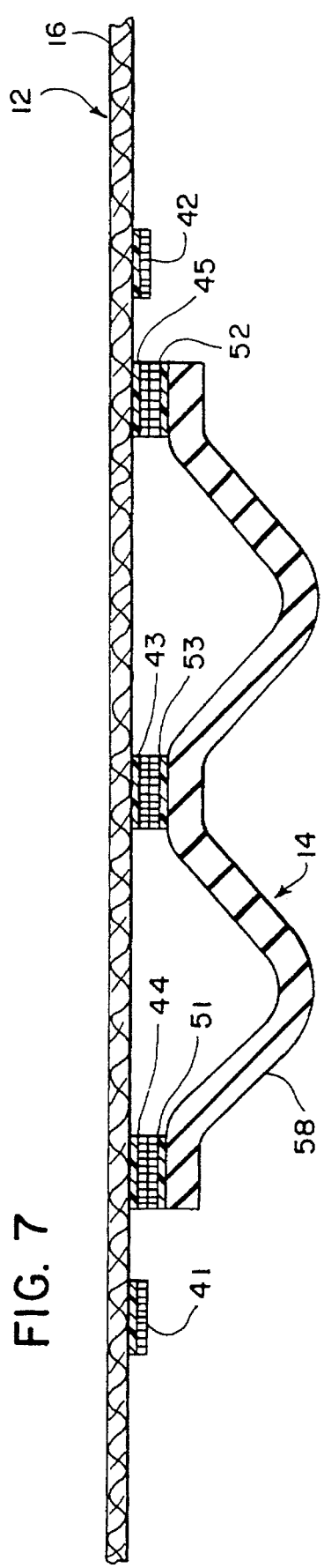

CONVERTIBLE SUPPORT BELT

BACKGROUND OF THE INVENTION

1. Field of the Invention

This invention relates to belts and in particular to abdominal support belts worn around the waist of a human user to increase the user's endurance and/or load carrying ability.

2. Discussion of the Prior Art

It has become popular for many different types of workers and sports enthusiasts to wear back support belts, either externally or internally of their clothing. Many of these belts are made of an open-weave elastic light weight breathable material and are relatively wide. Hook and loop type fastening material is provided on the ends of this type of belt to secure the ends of the belt together around the waist. It is also common to provide one or more elastic straps exterior of the belt and anchored in the middle of the back of the belt. These straps are pulled around the waist and have hook and loop type fastener material at their ends for attachment to mating hook and loop type fastener material on the exterior surface of the belt so as to provide a compression force on the users waist. Such belts are also sometimes used in conjunction with suspenders.

These belts have been made of lightweight, open mesh breathable elastic material so that they do not unnecessarily trap or retain body heat and are relatively cool for the user to wear. Other types of medical supports or waist wraps are made of neoprene, which is an insulating, non-breathable cushioning material.

At time it may be preferred to provide heat to the body in a certain area of the waist, especially in the area of the lower back, and at other times it may be preferred to cool that area. Prior supports or wraps provided one function or the other. The present invention provides a support which can accommodate either preference.

SUMMARY OF THE INVENTION

The present invention provides an abdominal support belt of the general type discussed above which is worn around the waist of a human user and secured to increase the intra-abdominal pressure of the user. The belt is provided with a foundation and a separate insulator insert. The foundation is made of an open-weave, light weight breathable woven fabric material which is elastic in the circumferential direction around the user's waist. The insert is releasably secured against an interior surface of the foundation and is removable so that the foundation can be worn without the insert. Thereby, in cold temperatures or when therapeutic warmth is desired, the insert can be secured to the foundation, or when it is desired to remain cool, it can be removed.

In one useful aspect, the interior surface of the foundation includes hook and loop type fastener material, and an exterior surface of the insert includes mating hook and loop type fastener material for removably securing the insert to the foundation. Thereby, the insert can be secured to and released from the foundation with ease, and the fastener material does not interfere with wearing the foundation without the insert in place.

Preferably, the fastener material on the foundation is located in a central rear area of the foundation when the belt is secured around a user's waist. With the insert secured in this position, warmth can be generated and maintained in the lower back area, where it is sometimes prescribed.

In another useful aspect, the insert is preferably made of a circumferentially elastic material and hook and loop type fastener material on the insert includes three spaced-apart vertically oriented strips of the fastener material including a first strip adjacent to one vertical edge of the insert, a second strip adjacent to the opposite vertical edge of the insert and a third strip disposed approximately halfway between the first and second strips. The hook and loop type fastener material on the foundation includes first, second and third spaced apart vertically oriented strips for releasably engaging the corresponding first, second and third strips on the insert. Thereby, as the foundation is stretched around a user's waist, the insert stretches outwardly from the third strip, along with the foundation, so as to conform to the user's waist.

In this regard, the fastener material on the foundation may include fourth and fifth vertically oriented strips, the strips being spaced apart from each other and both strips being inside of the first and second strips on the foundation. This way, when so much stretching of the insert is required that it would cause the ends of the insert to become detached from the foundation, the first and second strips on the insert can be releasably attached to the fourth and fifth strips, respectively, to reduce the amount of stretching of the insert and therefore maintain it attached to the foundation.

BRIEF DESCRIPTION OF THE DRAWINGS

FIG. 6 is a view similar to FIG. 5 but shown with the belt laid flat and for the entire length of the insert; and FIG. 7 is a view similar to FIG. 6 but with the insert shown attached to the belt in a different position.

DETAILED DESCRIPTION OF THE PREFERRED EMBODIMENTS

Figure 1:
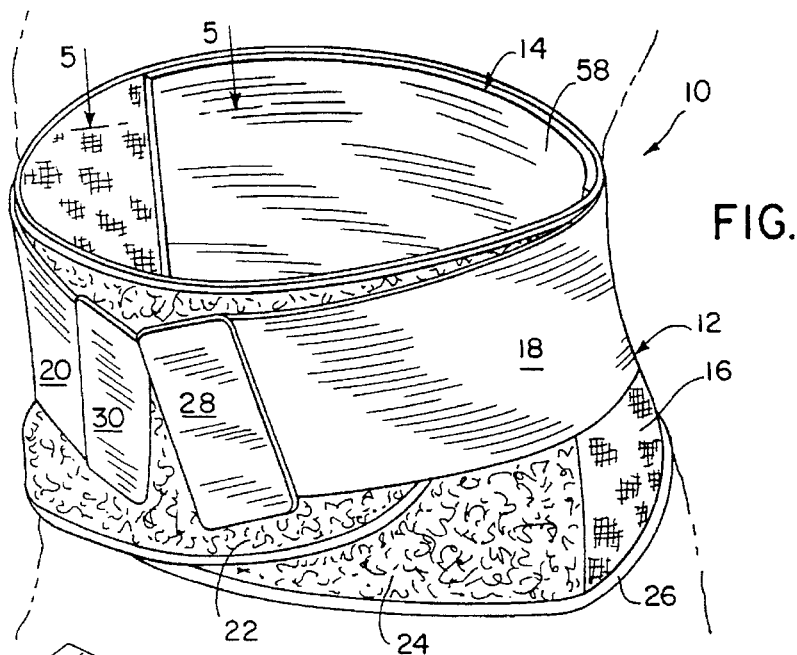
FIG. 1 is a perspective view of a belt of the invention shown wrapped around a user's waist, which is shown in phantom.
Figure 2:
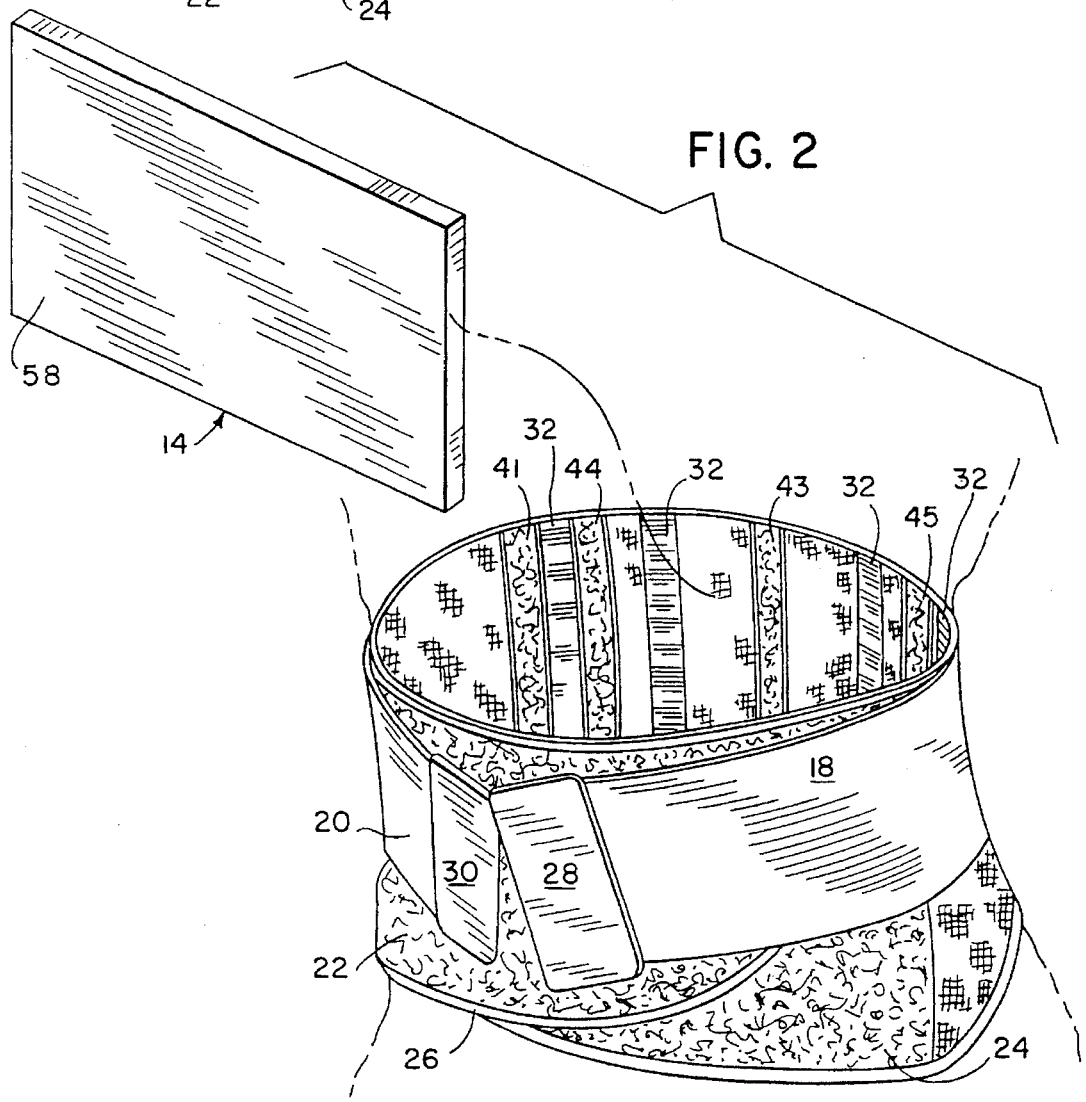
FIG. 2 is a perspective view similar to FIG. 1 shown with an insulation insert of the belt removed.

Referring to FIG. 1, an abdominal support belt 10 of the invention includes a foundation 12 and an insulation insert 14. The foundation 12 includes a body 16 and tensioning straps 18 and 20.

The body 16 has overlapping ends 22 and 24. The body 16 is made by first cutting an open-weave material which is elastic in the lengthwise or circumferential direction into the pattern of the body 16, including the ends 22 and 24. Such material is sometimes referred to as "power knit" and is commercially available from various manufacturers, including Guilford Mills of Greensboro, N.C. as Style No. 56373, from Liberty Fabrics of New York, N.Y. as Style No. 94309 or from Darlington Fabric of New York, N.Y. as Style No. 1231. The exterior sides of the overlapping ends 22 and 24 are then covered with patches of hook and loop type fastening material. In the preferred embodiment, the exterior sides of both ends 22 and 24 are covered with the loop type fastening material, and a patch of hook type fastening material is sewn onto the interior surface at the extreme end of end 22, to be engaged by the loop type material on end 24. A binding strip 26 is preferably sewn around the edges of the body 16 to prevent the edges from unravelling and for comfort and aesthetics.

Each of the straps 18 and 20, which are elastic in the circumferential direction, is secured by stitching to the rear center of the body 16. From that point, each strap 18 and 20 extends around the exterior side of the body 16 to respective ends 28 and 30. It should be understood that more than one elastic strap could be provided in each strap 18 and 20, extending from the central rear part of the body 16 to each respective end 28 and 30. Hook type fastener material is provided on the interior side of each end 28 and 30 for securing each end 28 and 30 to the loop type fastener material provided on the exterior side of end 22 of the body 16.

It should be noted that the foundation 12 as thus far described in detail is well known in the art. In addition, it is well known in the art to provide strips of batting 32 in the rear portion of the body 16 so as to provide vertical stiffness in the body 16.

Figure 3:
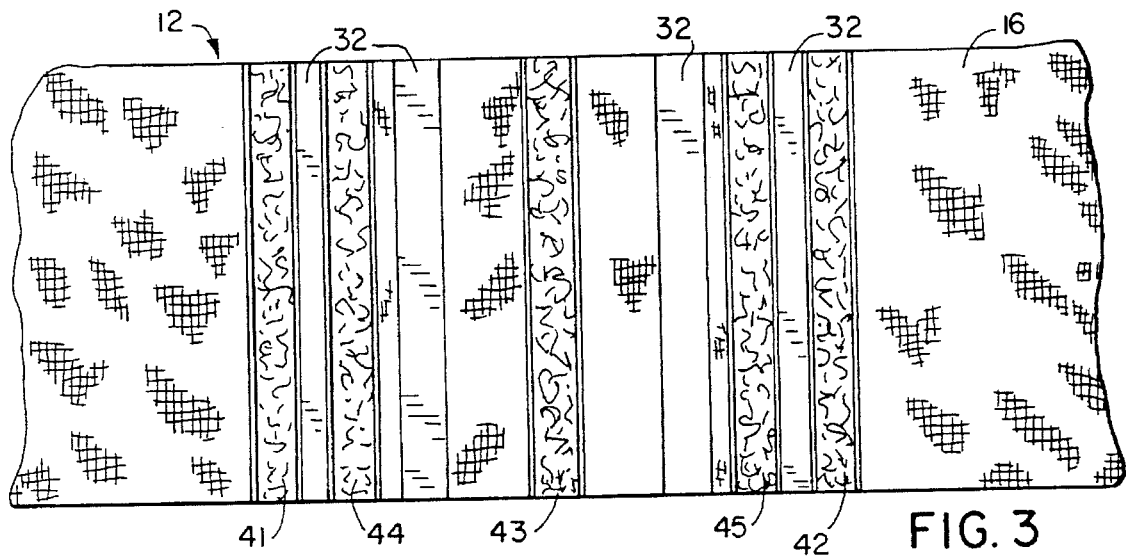
FIG. 3 is a partial plan view of the interior surface of the central portion of the belt, illustrated in a laid flat position.
Figure 4:
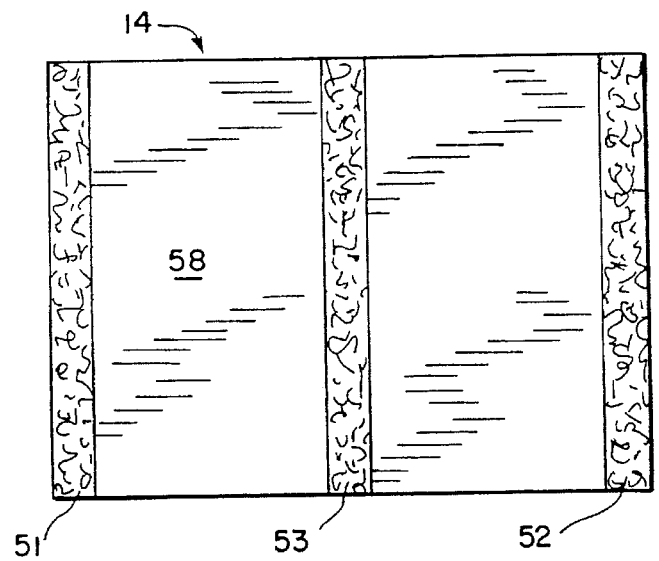
FIG. 4 is a plan view of the exterior side of the insert, illustrated in a laid flat position.
Figure 5:
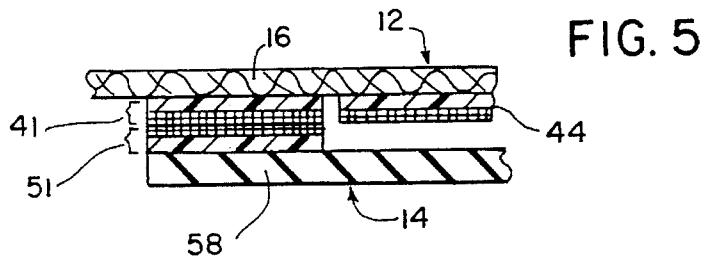
FIG. 5 is a cross-sectional view as viewed from the plane of the line 5—5 of FIG. 1.

It is not known, however, to provide a removable insulator insert 14 as part of the belt 10 as provided by this invention. Referring to FIG. 3, this is accomplished by providing vertically oriented strips of hook and loop type fastening material 41, 42, 43, 44 and 45 on the interior surface of the body 16 at the rear thereof and spaced apart.

Corresponding to the locations of the strips 41, 42, and 43 when the body 16 and insert 14 are laid flat, strips 51, 52 and 53 of hook type fastening material are stitched onto the exterior surface of a panel 58 of the insert 14. The panel 58 is preferably made of a flexible, soft and elastic insulating material so as to be comfortably worn by the user and retain heat against the user's body adjacent to the panel 58. Preferably, the panel 58 is a fabric covered neoprene, typically approximately 3 millimeters thick. Such material is well known and is desirable for its highly elastic properties and also because it is soft and is a good heat insulator. The fabric coverings for the neoprene may be any suitable fabric, preferably also elastic, such as nylon, Lycra™ or elastic terrycloth. In the preferred embodiment, terrycloth is preferred for the interior surface of the panel 58 so as to provide a soft, comfortable surface against the user, and one which would be useful to wick moisture away from the user's body. Any suitable fabric such as nylon may be used for the exterior surface of panel 58, since it is against the interior surface of the foundation 12. Neoprene suitable for making the panel 58 is available from Rubatex Corporation of Bedford, Va. under the commercial designation R-1400-N. However, it should be understood that aspects of the invention are not limited to making the panel 58 from neoprene materials, and that other flexible web materials could be used including other types of closed cell and open cell foam materials as well as non-foam sheet materials and elastic and inelastic materials. For example, if an inelastic material, were used, the panel 58 could be secured to the center of the body 16 using only the strips 43 and 53, which would allow the body 16 to stretch since the ends of the panel 58 would not be secured to the body 16.

Referring to FIGS. 6 and 7, in which the batting 32 is not shown for clarity, since the panel 58 has considerable elasticity in the circumferential direction, the strips 51, 52 and 53 can be positioned on it so that they register with the respective strips 41, 42 and 43 on the foundation 12 when both the foundation 12 and the insert 14 are relaxed and laid flat as shown in FIG. 6. In most instances, the insert 14 will stretch with the foundation 12 when the ends of the foundation 12 are secured around the user's waist. However, should the foundation 12 be required to stretch so much that the hook type fasteners 51 and 52 of the insert 14 become detached from the loop type fasteners 41 and 42 of the foundation 12, the strips 51 and 52 can be secured respectively to the strips 44 and 45 as shown in FIG. 7, so that the insert 14 folds between the strips 51 and 53 and between 52 and 53 when the foundation 12 is relaxed and laid flat. Then, when the foundation 12 is stretched around the user's waist, the insert 14 will remain attached because it stretches less and will assume a shape as shown in FIG. 6, so as to lay generally flat against the user's body as the belt 10 curves around the user's body.

Therefore, on hot days or when coolness is desired, insert 14 can be removed from the belt 10 and the belt 10 worn comfortably without it. Thus, it is preferred that the strips 41, 42, 43, 44 and 45 be of the loop type as that type of fastener is more comfortable to be worn against the user than is the hook type. That being the case, the hook type fastener material would be provided on the insert 14 as the strips 51, 52 and 53.

On cold days, or when additional therapeutic warmth is desired, the insert 14 can be secured to the foundation 12 as shown in FIG. 6 or FIG. 7, and the belt 10 worn by the user with the insert 14 in place as shown in FIG. 1.

Preferred embodiments of the invention have been shown and described in considerable detail. Many modifications and variations of the preferred embodiments will be apparent to those skilled in the art. Therefore, the invention should not be limited to the embodiments described or illustrated, but should be defined by the claims which follow.

I claim:

1. In an abdominal support belt of the type which is worn around the waist of a human user and secured to increase the intra-abdominal pressure of said user, said belt having an interior side facing said user and an exterior side facing away from said user, the improvement wherein said belt includes a foundation and an insulator insert, said foundation being made of an open-weave, light weight breathable woven fabric material which is elastic in the circumferential direction around said user's waist and said insert is releasably secured against an interior surface of said foundation, said insert being removable from said interior surface of said foundation, said interior surface of said foundation including five spaced-apart vertically oriented strips of hook and loop type fastener material including a first strip adjacent to one vertical edge of said insert, a second strip adjacent to the opposite vertical edge of said insert, a third strip disposed approximately halfway between said first and second strips and fourth and fifth vertically oriented strips, said fourth and fifth strips being spaced apart from each other and both said strips being inside of the first and second strips on the foundation, and an exterior surface of said insert including three spaced-apart vertically oriented strips of mating hook and loop type fastener material for removably securing said insert to said foundation including a first strip adjacent to one vertical edge of said insert, a second strip adjacent to the opposite vertical edge of said insert and a third strip disposed approximately halfway between said first and second strips for releasably engaging the corresponding first, second and third strips on said foundation, wherein said three strips on said insert may be placed in registration with said first, second and third strips on said foundation when said foundation and said insert are laid flat and in a relaxed state, wherein the first and second strips on the insert can be releasably attached to said fourth and fifth strips, respectively, and wherein said insert forms folds between said first and third and between said second and third strips when said first, second and third strips of said insert are secured to said fourth, fifth and third strips of said foundation, respectively, when said foundation is laid flat in a relaxed state.

2. The improvement as claimed in claim 1, wherein said insert is secured at the central rear portion of the foundation.

3. The improvement as claimed in claim 1, wherein said insert is made of an elastic material.

4. The improvement as claimed in claim 3, wherein said elastic material is fabric covered neoprene.

\* \* \* \* \*